(12) United States Patent
Utsunomiya

(10) Patent No.: US 9,601,090 B2
(45) Date of Patent: Mar. 21, 2017

(54) GRAPH DISPLAY PROCESSING SYSTEM

(71) Applicant: SHIMADZU CORPORATION, Kyoto-shi, Kyoto (JP)

(72) Inventor: Shin-ichi Utsunomiya, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 194 days.

(21) Appl. No.: 14/024,914

(22) Filed: Sep. 12, 2013

(65) Prior Publication Data
US 2014/0078182 A1    Mar. 20, 2014

(30) Foreign Application Priority Data

Sep. 14, 2012 (JP) ................................. 2012-202325
Apr. 26, 2013 (JP) ................................. 2013-093280

(51) Int. Cl.
*G09G 5/37* (2006.01)
*G06F 3/048* (2013.01)
(Continued)

(52) U.S. Cl.
CPC ............. *G09G 5/37* (2013.01); *G06F 3/0481* (2013.01); *G09G 5/14* (2013.01); *G01N 30/72* (2013.01);
(Continued)

(58) Field of Classification Search
CPC ............... G01N 30/72; G01N 30/8651; G01N 30/8696; G06F 3/0481; G09G 2340/0407;
(Continued)

(56) References Cited

U.S. PATENT DOCUMENTS 5,694,123 A * 12/1997 Selker .................. G06F 1/1616
341/20
2005/0060658 A1* 3/2005 Tsukiori ........................ 715/765
(Continued)

FOREIGN PATENT DOCUMENTS

| JP | 2006-318199 A | 11/2006 |
| JP | 2008-52580 A | 3/2008 |
| JP | 2010-54318 A | 3/2010 |

OTHER PUBLICATIONS

Machine translated JP2006-318199, Kamata, Nov. 24, 2006.*
Machine translated JP2008-052580, Toyoda et al., Mar. 6, 2008.*

*Primary Examiner* — Sing-Wai Wu
(74) *Attorney, Agent, or Firm* — Sughrue Mion, PLLC

(57) ABSTRACT

After an operator has roughly moved a plurality of windows 101-103, with a graph (e.g. spectrum) placed in each window, to desired positions by a manual operation, initial positional coordinates of each window are acquired. The operator also makes an input of the selection of an arrangement pattern (e.g. vertical arrangement). According to the selected arrangement pattern and the number of windows, the sizes of display areas to be formed by dividing a main display frame 100 are calculated, and the display position of each window is also determined. Then, the display order of the windows is calculated from the relative positional relationship of the windows revealed from their initial positional coordinates, and a display screen is eventually formed by resizing each window so as to fit it to the size of the display area and then arranging the windows in the calculated display order.

12 Claims, 12 Drawing Sheets

(51) Int. Cl.
  *G09G 5/14* (2006.01)
  *G06F 3/0481* (2013.01)
  *G01N 30/72* (2006.01)
  *G01N 30/86* (2006.01)

(52) U.S. Cl.
  CPC ..... *G01N 30/8651* (2013.01); *G01N 30/8696* (2013.01); *G09G 2340/0407* (2013.01); *G09G 2340/0464* (2013.01); *G09G 2340/14* (2013.01)

(58) Field of Classification Search
  CPC ....... G09G 2340/0464; G09G 2340/14; G09G 5/14; G09G 5/37
  See application file for complete search history.

(56) References Cited

U.S. PATENT DOCUMENTS

2010/0134825 A1* 6/2010 Pierce et al. ............... 358/1.15
2011/0148881 A1* 6/2011 Kageyama ................. 345/440

* cited by examiner

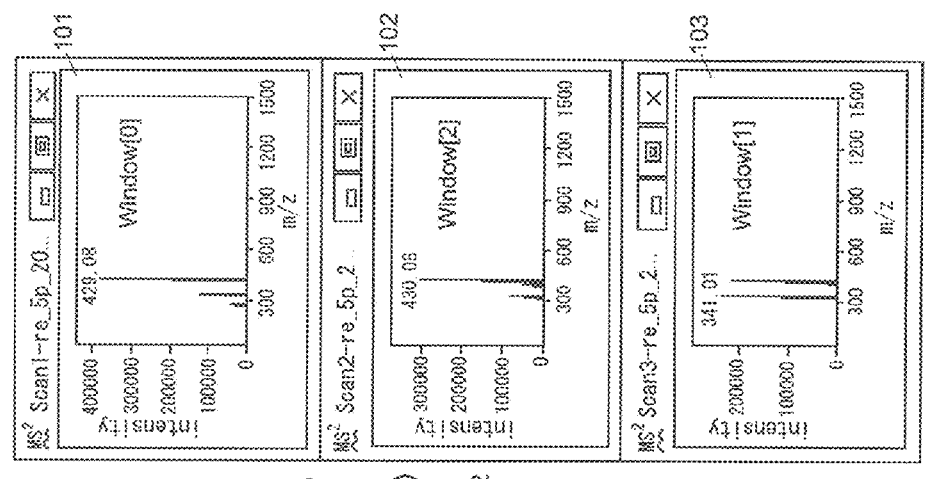
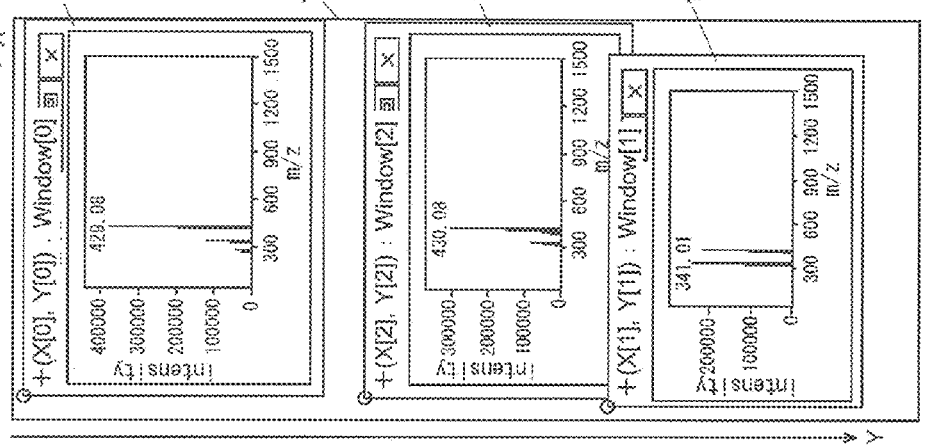
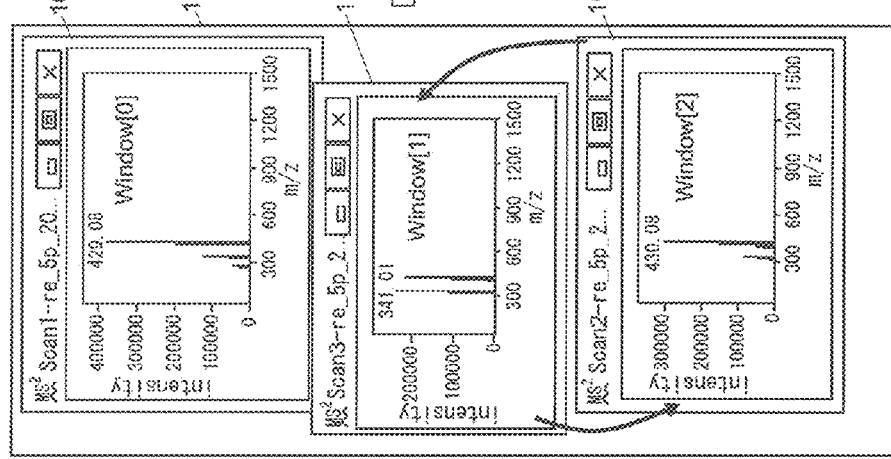

Fig. 4
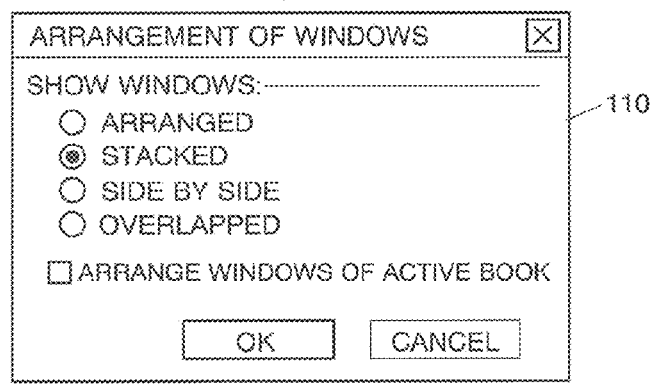
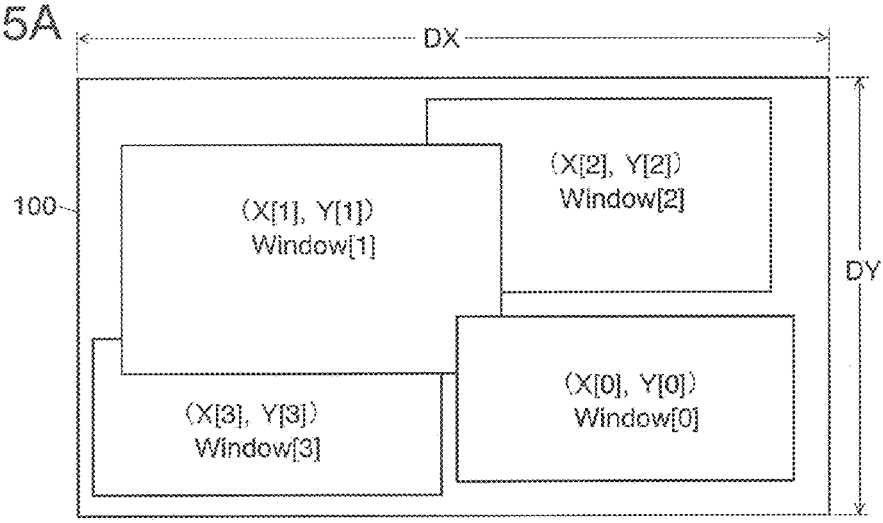
Fig. 5A
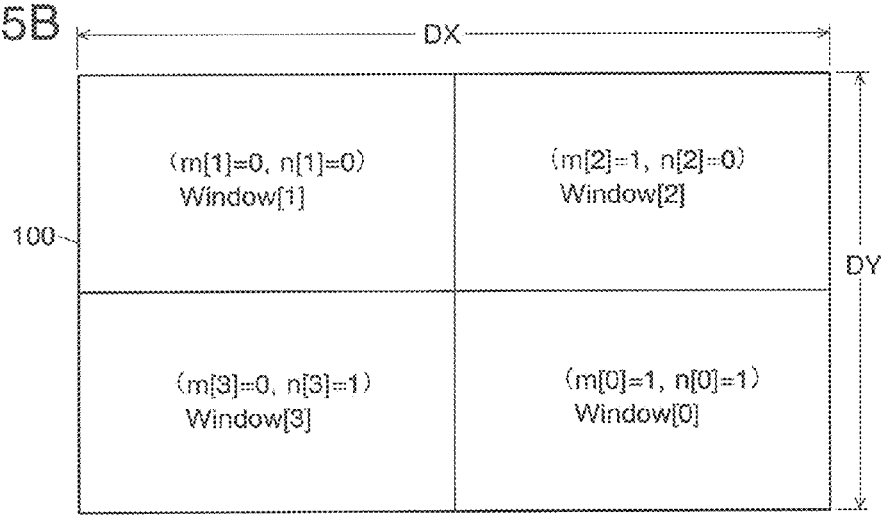
Fig. 5B

Fig. 6A BEFORE ARRANGEMENT
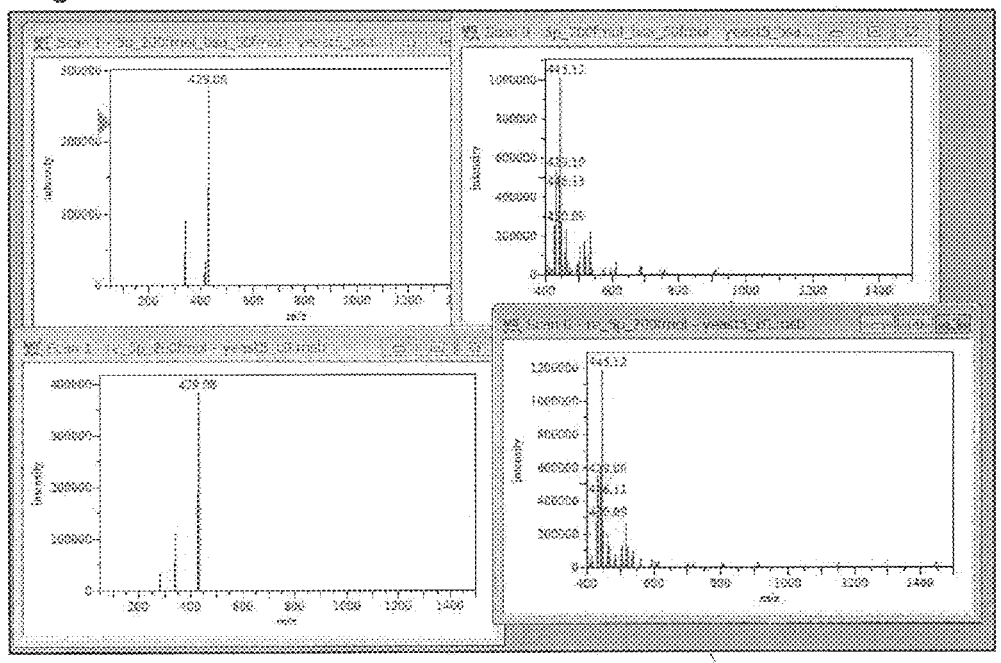
Fig. 6B AFTER ARRANGEMENT
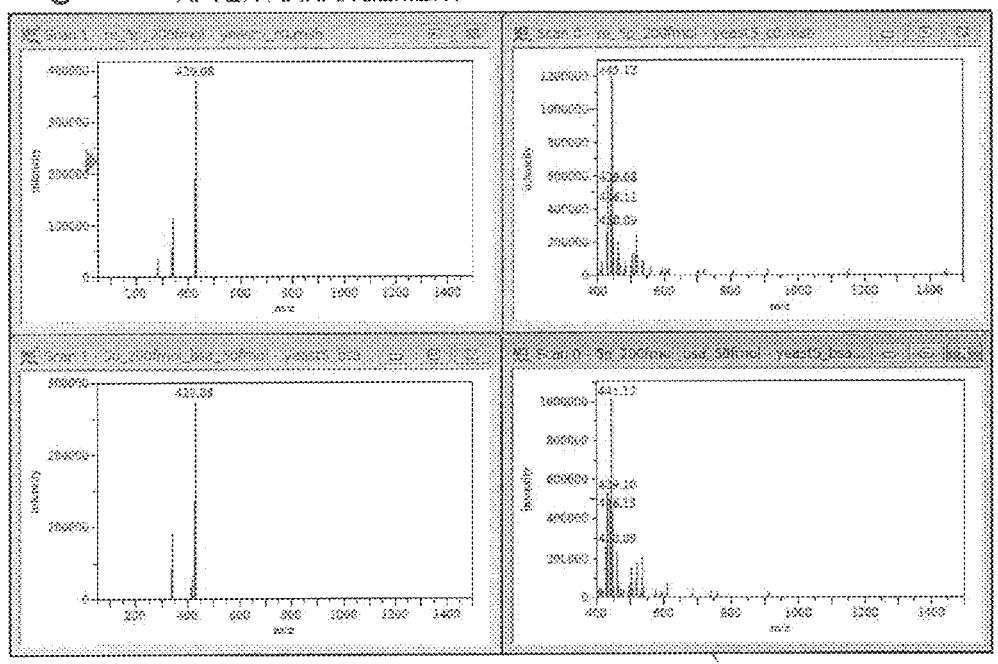

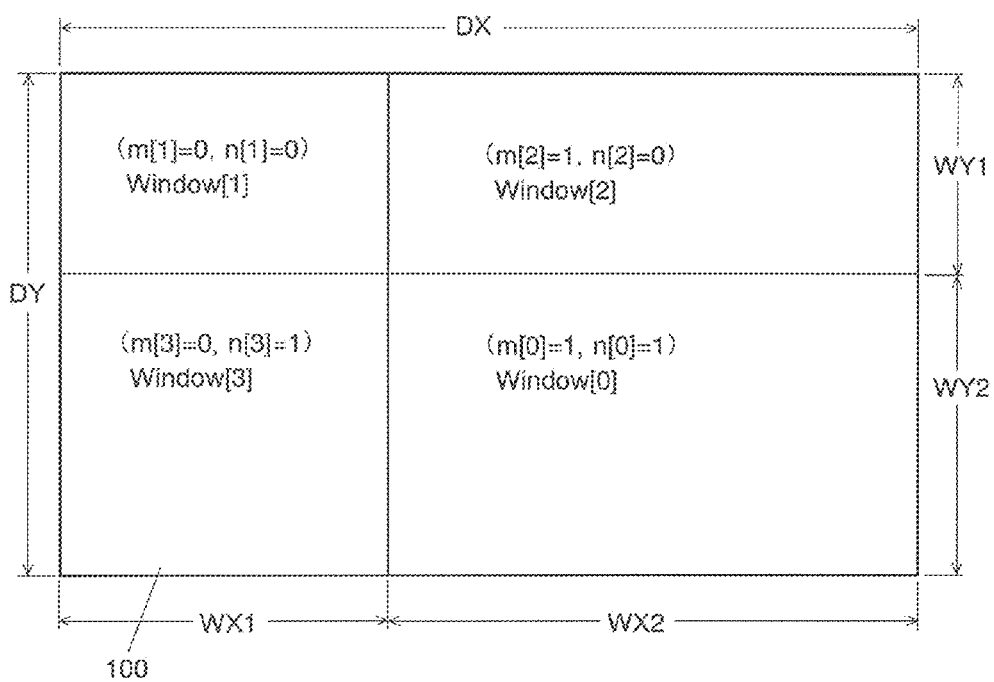

BEFORE ARRANGEMENT

AFTER ARRANGEMENT

BEFORE ARRANGEMENT

AFTER ARRANGEMENT

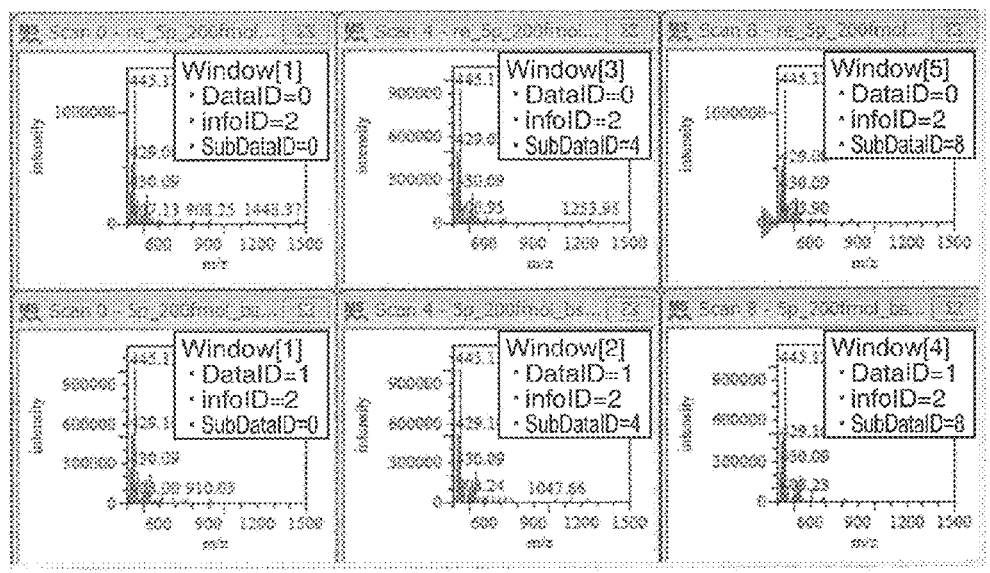

GRAPH DISPLAY PROCESSING SYSTEM

TECHNICAL FIELD

The present invention relates to a graph display processing system for showing, on a display screen, various kinds of graphs (such as a chromatogram, spectrum, or mapping image) created on the basis of data collected with various kinds of analyzing or measuring systems, such as a liquid chromatograph mass spectrometer or a gas chromatograph mass spectrometer.

BACKGROUND ART

A liquid chromatograph mass spectrometer (LC/MS) or gas chromatograph mass spectrometer (GC/MS), which is composed of a chromatograph and a mass spectrometer, is capable of creating a mass spectrum at an arbitrary point in time based on data obtained by an analysis on a sample, as well as creating a chromatogram, such as a total ion chromatogram or a mass chromatogram for an arbitrary mass-to-charge ratio m/z. With an ultraviolet-visible spectrophotometer, Fourier transform infrared spectrophotometer or similar analyzing system, it is possible to create an absorption spectrum, reflection spectrum or similar spectrum based on data obtained by an analysis on a sample.

In recent years, the data processing in those types of analyzing systems has been predominantly performed by a multi-purpose personal computer. In such a system, various kinds of data analyses are performed and their results are displayed by executing a dedicated controlling and processing application software program installed in a personal computer. The results of those analyses are not only presented in-situ but can also be pasted in a document, such as a written report or presentation material.

When it is necessary to examine an analysis result obtained by previously described analyzing systems or compare the results of analyses performed on a plurality of samples, an analysis operator appropriately selects spectra, chromatograms or other kinds of graphs as needed and makes them shown on a screen so that the operator can closely examine the waveform of a portion in question of the graph or compare a plurality of waveform shapes. To allow such analytical work to be performed smoothly, conventional analyzing systems have the function of showing a plurality of windows on a monitor screen, with a chromatogram, mass spectrum or similar graph placed in each window, and allowing the analysis operator to appropriately change the size and position of each window so that the comparison of the graphs or other tasks can be easily performed.

For example, Patent Documents 1 and 2 disclose a display control system which displays a graph, such as a chromatogram or mass spectrum, in each of a plurality of areas formed by dividing the inner area of one large window (those areas are called "tile windows" in Patent Document 2). In this type of display form, users can easily change the size of each area by performing a drag operation on the frames separating the areas, using a mouse or similar pointing device. However, transposing the graphs individually shown on the areas requires cumbersome operations, and in this respect, it can be said that the degree of freedom for the graph arrangement is low. This type of display is normally realized by a software system called the "tiling window manager."

Patent Document 3 discloses another type of commonly known display form, in which one completely independent window is created for each graph. This type of display system allows users to move each window to an arbitrary position on the display screen by a drag-and-drop operation using a pointing device. The resizing of each window is also easy. Due to these features, this system can be said to have a higher degree of freedom of display and operation than the aforementioned tiling-window display system. Such a display system is normally realized by a software system called the "compositing window manager."

Even in the case where graphs are placed on the respective independent windows as in the latter system, if users want to compare the results of analyses performed on the same sample under different conditions or to compare the result of a target sample with that of a control sample, it is necessary, for example, to resize the windows, with the graphs to be compared displayed thereon, to the same size and arrange them side by side or in a vertically stacked form. In many application software products which are capable of this kind of display control, the aforementioned arrangement is realized by a process including the following operations and steps.

(1) First, among a plurality of windows on the display screen, the operator sequentially performs a click or similar operation using a pointing device on the windows shown on the display screen to select target windows in an order in which the windows should be arranged. Upon this input operation, the computer internally stores the order of selection of the windows as "window arrangement order information."

(2) Next, the operator specifies an arrangement pattern, such as a longitudinal (vertical) or lateral (horizontal) direction, through the selection of a menu item or similar operation. Upon this input operation, the computer internally converts the window arrangement order information into "spatial window arrangement information", which is necessary for arranging the windows, according to the specified arrangement pattern.

(3) According to the calculated spatial window arrangement information, the computer internally re-orders and arranges the target windows, and eventually shows them on the screen of a display unit.

FIGS. 9A and 9B show one example of the operation of arranging the windows according to the aforementioned procedure. In the example, three windows 101, 102 and 103, in each of which an MS/MS spectrum created by a mass spectrometer is placed, are to be vertically arranged on the display in order of the scan number ("Scan") indicating the order of the mass scan. Suppose that the initial arrangement of the windows 101-103 on the display screen is as shown in FIG. 9A: windows 101-103 vary in size and partially overlap each other, without being arranged in order. On this screen, the operator clicks each of the windows 101-103 in the order in which the windows should be arranged. Now, suppose that the three windows 101-103 have been clicked in the order of [1], [2] and [3] as indicated on the right side of FIG. 9A.

Next, the operator performs a predetermined operation, whereupon an arrangement pattern specification dialogue 110 as shown in FIG. 4 appears on the display screen. On this dialogue 110, the operator selects one of the options of the arrangement pattern as desired. Now, suppose that a "Show Windows Stacked" option has been selected and is specified on the arrangement pattern specification dialogue 110. According to this selection, windows 101-103 are adjusted to the same size and arranged in the specified order, as shown in FIG. 9B. If a "Show Windows Side by Side" option is selected and specified on the arrangement pattern specification dialogue 110, the three windows 101-103, with the lateral width adjusted to the same value, are arranged side by side on the display screen.

However, the conventional process of arranging the windows by the previously described operations and processes has the following problems.

(1) The operation of specifying the arrangement order of the windows by the operator is performed along the time series, while the actual arrangement of the windows is in accordance with the spatial order on the display screen. The correspondence between the temporal sequence information and the spatial sequence information is definitely determined in the software, but operators often incorrectly recognize this correspondence. For example, in the previously described case of showing the windows in the vertically stacked form, the windows will be sequentially arranged in the bottom-to-top direction on the screen according to the temporal order of the click operation (the earlier the click, the lower the position). However, some operators erroneously assume that the windows will be sequentially arranged in the top-to-bottom direction. In this case, the arrangement result will be opposite to what is intended by the operator.

(2) When sequentially selecting a plurality of windows, the operator must repeat the selecting operation while memorizing the order of the windows which have already been selected. If there are many windows to be arranged, the operator will easily make mistakes, such as an omission or double selection of a window, so that it will be more difficult to have the windows arranged in the correct order which fully reflects the intention of the operator. Furthermore, if an error of the order of selection is found in the middle of the process of sequentially selecting the windows, the operator must restart the entire selecting operation from the beginning, which is cumbersome and time consuming. The lack of a means for easily correcting the order of selection in the middle of the process also puts a psychological burden on the operator.

(3) In the case of a one-dimensional arrangement, such as the vertical or horizontal arrangement, it is comparatively easy to recognize the correspondence between the temporal sequence information indicating the order of selection of the windows and the spatial sequence information indicating the order of arrangement of the windows. However, in the case of two-dimensionally arranging the windows in the form of a matrix with specified numbers of rows and columns, the operation is so complex that it is difficult for operators to intuitively understand the operation. This is because there are several possible rules for selecting windows, and the operator needs to memorize which of those selection rules is specified. For example, the rule may require the windows to be selected in such an order that each row is sequentially selected in the top-to-bottom direction and the windows to be placed in the selected row are individually and sequentially selected in the left-to-right direction. Therefore, the operability in the case of the two-dimensional arrangement is not very high. It is also difficult to prevent errors in the operations.

BACKGROUND ART DOCUMENT

Patent Document

Patent Document 1: JP-A 2006-318199
Patent Document 2: JP-A 2008-52580
Patent Document 3: JP-A 2010-54318

SUMMARY OF THE INVENTION

Problem to be Solved by the Invention

The present invention has been developed to solve the previously described problem, and its primary objective is to provide a graph display processing system for displaying a plurality of windows in a desired arrangement form, with each window having a graph (e.g. a spectrum, a chromatogram, or a mapping image on which data values are represented by the luminance of the image points) placed therein, in which the system operability is improved so as to enhance the working efficiency and to prevent an erroneous operation, i.e. to prevent windows from being arranged in an unintended way.

Means for Solving the Problems

The first aspect of the present invention aimed at solving the aforementioned problem is a graph display processing system for performing a process in which each of a plurality of graphs created on the basis of data collected by an analysis or measurement on a sample is placed in one of a plurality of windows and the windows are shown on a display screen, including:

a) an initial position specifier for moving each of the plurality of windows on the display screen to an arbitrary position according to an operation by an operator;

b) an initial position information acquirer for acquiring, as initial position information, information on the position of the plurality of windows after being moved by the initial position specifier;

c) an arrangement pattern specifier for allowing the operator to perform an operation for specifying an arrangement pattern on the display screen;

d) a post-arrangement display information calculator for calculating a display size and display position information of each window after arrangement, based on the initial position information of each window acquired by the initial position information acquirer and the arrangement pattern specified by the arrangement pattern specifier; and e) an arrangement processor for resizing each window according to the display size calculated by the post-arrangement display information calculator, and for displaying the resized windows in an arranged form according to the post-arrangement display position information calculated by the post-arrangement display information calculator.

In the graph display processing system according to the present invention, the initial position specifier includes, for example, a pointing device (such as a mouse) and a user interface for detecting a drag and drop operation of the device by an operator and for moving a window on the display screen based on information relating to the amount, direction and other elements of the detected operation.

To arrange a plurality of windows each of which has one or more graphs shown therein, the operator moves the windows on the display screen by using the initial position specifier so that each window is roughly located at the desired position. Since the windows at this stage may possibly vary in size, it is preferable to previously designate one of the corners of the roughly rectangular frame of each window as a representative point of that window so that the schematic layout of the windows can be determined based on the position of their representative points. Thus, in the first aspect of the present invention, the pre-arrangement initial position of the windows according to an operation of the operator is shown on the display screen, and the operator can specify rough arrangement of the windows while visually checking the display screen. Therefore, the operator can easily foresee how the windows will be arranged after the arranging operation is executed, and will not incorrectly recognize the arrangement direction as in the case of the conventional technique in which the arrangement order is specified in order of the click operation.

After the initial positions of the plurality of windows are fixed according to the previously described operation by the operator, the initial position information acquirer obtains the position information of the windows as initial position information. For example, the positional coordinates of the representative point of each window can be used as the initial position information. The operator also specifies the arrangement pattern through the arrangement pattern specifier. The "arrangement pattern" may include the arrangement direction (vertical or horizontal) in the case of the one-dimensional arrangement or the numbers of rows and columns in the case of the two-dimensional arrangement.

After the arrangement pattern is selected, the post-arrangement display information calculator determines the display position information of each window by partitioning a display frame, which is previously assigned for the arrangement of a plurality of windows, according to the arrangement pattern and the number of windows to be displayed. The calculator also determines the display size of each window. The arrangement processor resizes each window together with the graph according to the calculated display size, then arranges the resized windows according to the post-arrangement display position information, and produces the images of the arranged windows on the display screen.

The aforementioned display frame in which a plurality of windows are to be placed may have a fixed size. However, it will be more convenient if operators can freely adjust the frame size. Accordingly, the system according to the first aspect of the present invention further includes a display frame specifier for allowing an operator to specify, on the display screen, a display frame in which the plurality of windows are to be arranged, and the post-arrangement display information calculator partitions the display frame specified through the display frame specifier into a plurality of areas according to the number of windows to be displayed and the arrangement pattern, and calculates the display size and the display position information of each window. This configuration can also be adopted in a system according to any one of the second through fourth aspects of the present invention, which will be described later.

For example, when the operator wants the graphs placed in the plurality of windows to be viewed together with another kind of information on the display screen, the previously described function can be used to adjust the size of the display frame so that the frame will not overlap the aforementioned information. Furthermore, the size of the display frame can be appropriately adjusted according to the kind or other features of the graph placed in each window, so as to obtain an aspect ratio that makes the graph easy to view or look natural in appearance.

In general, when a plurality of windows with the same kind of graphs individually placed therein are arranged on the display screen, the graphs will often be easy to view if all the windows are adjusted to the same size. In that sense, the previously described configuration is sufficient for many cases. However, when a plurality of windows with different kinds of graphs (e.g. chromatograms and mapping images) placed therein are arranged, differently adjusting the size of each window according to the kind of graph may be convenient for analytical work.

Accordingly, in one preferable mode of the system according to the first aspect of the present invention, the arrangement pattern specifier is configured so that size specification information to be used for adjusting the size of each area formed by partitioning the display frame can be specified, and the post-arrangement display information calculator partitions the display frame into a plurality of areas based on the size specification information. For example, the size specification information may be the ratio between the height and width of each of the windows arranged in the vertical and horizontal directions.

For example, if there is a window which shows a particularly important graph or an extremely fine graph containing a larger amount of information, the above function can be used to assign the largest size to that window so as to make the display suitable for analytical work. Furthermore, in the case of creating an output of the displayed result on a piece of paper or other media for reporting or other purposes, a well-balanced, finely-presentable report can be promptly created with simple operations.

When an arrangement pattern which has been once selected by an operator is repeatedly used, or when a default arrangement pattern prepared in the system is used, it is unnecessary to provide the arrangement pattern specifier.

Taking this into account, the second aspect of the present invention aimed at solving the previously described problem provides a graph display processing system for performing a process in which each of a plurality of graphs created on the basis of data collected by an analysis or measurement on a sample is placed in one of a plurality of windows and the windows are shown according to a specific arrangement pattern on a display screen, including:

a) an initial position specifier for moving each of the plurality of windows on the display screen to an arbitrary position according to an operation by an operator;

b) an initial position information acquirer for acquiring, as initial position information, information on the position of the plurality of windows after being moved by the initial position specifier;

c) a post-arrangement display information calculator for calculating a display size and display position information of each window after arrangement, based on the initial position information of each window acquired by the initial position information acquirer and the arrangement pattern specified beforehand; and d) an arrangement processor for resizing each window according to the display size calculated by the post-arrangement display information calculator, and for displaying the resized windows in an arranged form according to the post-arrangement display position information calculated by the post-arrangement display information calculator.

In this system, when the display size and the display position information of each window after arrangement are to be calculated, the post-arrangement display information calculator does not refer to the arrangement pattern specified by the arrangement pattern specifier, but refers to a previously specified arrangement pattern.

The system according to the second aspect of the present invention is advantageous in that operators do not always need to specify the arrangement pattern. However, for example, when the number or kind of graphs to be displayed has been changed, it may be necessary to change the arrangement pattern to be used. In particular, if this mode-changing operation requires the operator to specify the numbers of rows and columns for determining the arrangement pattern, the operation becomes rather complex for the operator and an error is likely to occur.

Taking this into account, the third aspect of the present invention aimed at solving the aforementioned problem provides a graph display processing system for performing a process in which each of a plurality of graphs created on the basis of data collected by an analysis or measurement on a sample is placed in one of a plurality of windows and the windows are shown on a display screen, including:

a) an initial position specifier for moving each of the plurality of windows on the display screen to an arbitrary position according to an operation by an operator;

b) an initial position information acquirer for acquiring, as initial position information, information on the position of the plurality of windows after being moved by the initial position specifier;

c) an arrangement pattern determiner for collecting window property information for each and every one of the plurality of windows shown on the display screen, the window property information given to each window beforehand and including at least information indicating the kind and origin of the graph placed in each window, and for determining an arrangement pattern based on the collected window property information corresponding to the plurality of windows;

d) a post-arrangement display information calculator for calculating a display size and display position information of each window after arrangement, based on the initial position information of each window acquired by the initial position information acquirer and the arrangement pattern determined by the arrangement pattern determiner; and e) an arrangement processor for resizing each window according to the display size calculated by the post-arrangement display information calculator, and for displaying the resized windows in an arranged form according to the post-arrangement display position information calculated by the post-arrangement display information calculator.

The window property information includes at least information indicating the kind of graph placed in the window (e.g. chromatogram, mass spectrum, absorption spectrum, two-dimensional mapping, etc.) and information indicating the origin of the graph (e.g. the type of an apparatus with which the original data used for creating the graph were obtained, or the kind of sample used). The window property information can be created automatically or manually at the point of creation of a window with one arbitrary graph placed therein, and be registered, for example, as a property linked with the window.

In the system according to the third aspect of the present invention, the arrangement pattern determiner collects window property information given to all the windows to be arranged, and automatically determines the arrangement pattern by analyzing the window property information. For example, it determines the numbers of rows and columns of a two-dimensional arrangement by analyzing the kind information and graph-origin information of the graph included in the window property information of all the windows. If it has been found that there are three kinds of graphs created from original data obtained from two kinds of samples, it is possible to use an arrangement pattern with three rows and two columns or two rows and three columns. The operator does not need to input the selection of the arrangement pattern or enter information which determines the arrangement pattern.

The fourth aspect of the present invention aimed at solving the aforementioned problem is a graph display processing system for performing a process in which each of a plurality of graphs created on the basis of data collected by an analysis or measurement on a sample is placed in one of a plurality of windows and the windows are shown on a display screen, including:

a) an arrangement rule determiner for collecting window property information for each and every one of the plurality of windows shown on the display screen, the window property information given to each window beforehand and including at least information indicating the kind and origin of the graph placed in each window, for determining an arrangement pattern based on the collected window property information corresponding to the plurality of windows, and for determining an arrangement order of each window based on the window property information;

b) a post-arrangement display information calculator for calculating a display size and display position information of each window after arrangement, based on the arrangement pattern and the arrangement order determined by the arrangement rule determiner; and c) an arrangement processor for resizing each window according to the display size calculated by the post-arrangement display information calculator, and for displaying the resized windows in an arranged form according to the post-arrangement display position information calculated by the post-arrangement display information calculator.

Unlike the first through third aspects of the present invention, the system according to the fourth aspect of the present invention does not have the initial position specifier, and therefore, does not require operators to perform the initial operation of roughly moving the windows. Instead of having operators perform the window-moving operation, the arrangement rule determiner automatically determines not only the arrangement pattern based on the window property information, but also the row number and column number to be assigned to each window according to the kind information and graph-origin information of the graph given to the window. Specific rules can be previously made about how to determine the order according to the kind information and graph-origin information of the graph, e.g. which kind of graph should be placed first if the kinds of graphs are chromatogram and mass spectrum. These rules may be made on the maker's side instead of being set by the user.

In case the display rules thus determined (e.g. the display order, or which kind of information is assigned to which of the horizontal and vertical directions in a two-dimensional arrangement pattern) do not agree with the intention of the user, it is preferable to provide the system with a display rule inverter for performing a post-processing according to a user operation, i.e. a means for transposing the rows and columns of a two-dimensional arrangement pattern, or for inverting the arrangement order in at least one of the row and column directions in the case of a two-dimensional arrangement pattern or the arrangement order in the case of a one-dimensional arrangement pattern.

Effect of the Invention

With the graph display processing system according to any one of the first through fourth aspects of the present invention, a plurality of windows each of which has a graph (e.g. a spectrum or chromatogram) placed therein can be displayed in a desired arrangement pattern by a simple operation method which operators can easily understand. Even if there are many windows to be displayed, the operation can be performed with fewer errors. Restarting the operation requires less time and labor. An arrangement with a complex display layout, such as a two-dimensional arrangement with a specified number of rows and a specified number of columns, can also be realized by a simple operation which can be easily and intuitively understood by operators.

The present invention is particularly effective in the field of diagnosing cancer or other diseases using an LC/MS or GC/MS. Such a diagnosis often includes a comparative analysis of a measurement result of a sample from a normal subject and that of a sample from a patient, or a search for common characteristics among the results of measurements of a plurality of samples. In many cases, such an analysis or search requires arranging a number of windows on a display screen and comparing various kinds of graphs placed in those windows, such as MS' spectra or chromatograms of a plurality of stages, two-dimensional mapping images with the two axes indicating the retention time and the mass-to-charge ratio, or results of a multivariate analysis or similar statistic analysis. In such cases, the graph display processing system according to the present invention provides a method which is easy to understand and simple to actually operate for operators, thus reducing the burden on the operators as well as improving their work efficiency. An improvement in the quality of analysis results can also be expected.

In the case of the graph display processing system according to the second aspect of the present invention, when an arrangement pattern which has been once selected by an operator is repeatedly used, or when a default arrangement pattern prepared in the system is used, the operator does not need to input the selection of the arrangement pattern or enter information which determines the arrangement pattern. Therefore, the burden on the operator is further reduced.

In the case of the graph display processing system according to the third aspect of the present invention, whatever kinds of graphs are placed in the windows, the operator does not need to input the selection of the arrangement pattern or enter information which determines the arrangement pattern. Therefore, the burden on the operator is further reduced.

In the case of the graph display processing system according to the fourth aspect of the present invention, the initial operation by the operator for roughly moving the windows is also unnecessary, so that the burden on the operator is even further reduced and the windows can be displayed in an arranged form by extremely simple operations.

BRIEF DESCRIPTION OF THE DRAWINGS

FIGS. 3A-3C are model diagrams showing one example of the window arrangement process for displaying graphs in the LC/MS system of the first embodiment.

FIG. 4 shows one example of the arrangement pattern specification dialogue.

FIGS. 5A and 5B are explanatory diagrams showing a process of two-dimensionally arranging a plurality of windows in the LC/MS system of the first embodiment.

FIGS. 6A and 6B show one example of the process of two-dimensionally arranging a plurality of windows, with a mass spectrum placed in each window, in the LC/MS system of the first embodiment.

FIG. 7 is an explanatory diagram of a process of two-dimensionally arranging a plurality of windows, with the size of each window adjusted, in the LC/MS system of the first embodiment.

FIG. 16 shows one example of the process of two-dimensionally arranging a plurality of windows in an LC/MS system as a variation of the third embodiment.

FIGS. 17A-17C show an example of the window property information.

BEST MODE FOR CARRYING OUT THE INVENTION

First Embodiment

Figure 1:
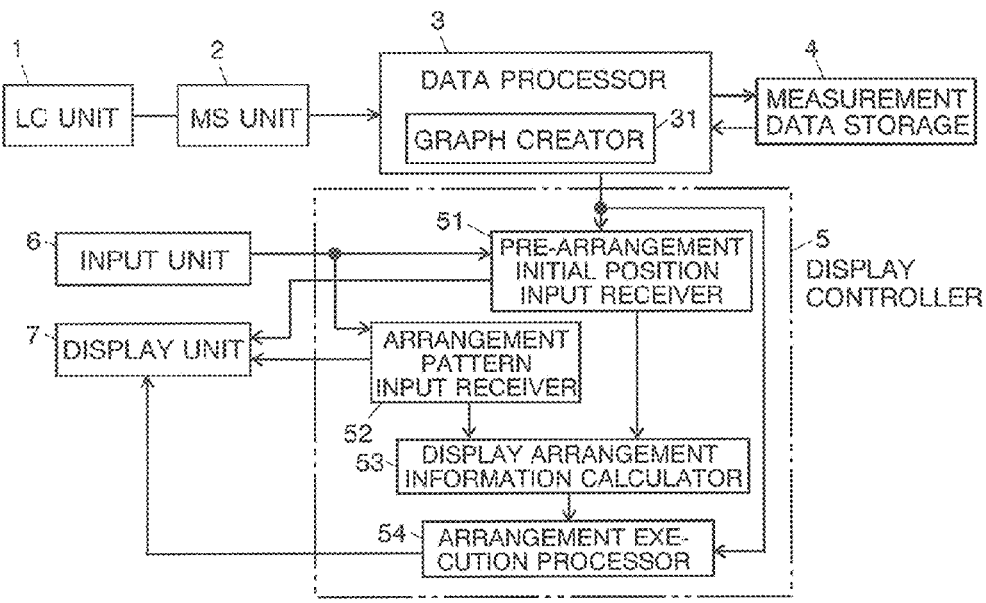
FIG. 1 is a configuration diagram showing the main components of an LC/MS system including a graph display processing system according to the first embodiment of the present invention.

One embodiment (first embodiment) of the LC/MS system including a graph display processing system according to the present invention is hereinafter described with reference to the attached drawings. FIG. 1 is a schematic diagram showing the main components of the LC/MS system of the first embodiment.

This LC/MS system includes a liquid chromatograph (LC unit) 1 for temporally separating the components contained in a sample, a mass spectrometer (MS unit) 2 for detecting each of the separated components individually according to their mass-to-charge ratios m/z, a data processor 3 for processing data obtained with the MS unit 2, a measurement data storage 4 for storing measurement data, a display controller 5 for performing a display control characteristic of this system, an input unit 6 consisting of a keyboard and a pointing device (e.g. mouse), and a display unit 7 serving as a display monitor. The data processor 3 includes a graph creator 31 for creating graphs, such as mass spectra or various kinds of chromatograms, based on the measurement data. The display controller 5 includes a pre-arrangement initial position input receiver 51, an arrangement pattern input receiver 52, a display arrangement information calculator 53, an arrangement execution processor 54, and other functional blocks.

The data processor 3, the measurement data storage 4 and the display controller 5 can be embodied by using a personal computer as the hardware resource and executing a preinstalled, dedicated controlling and processing application software program on that personal computer.

The LC/MS system of the first embodiment acquires measurement data and stores them in the measurement data storage 4 as follows: When a sample is introduced into the LC unit 1, the components contained in the sample are temporally separated while passing through a column (not shown), to be eventually eluted from the column. The MS unit 2 performs an SIM measurement; i.e., the unit repeatedly measures the signal intensity corresponding to the amount of ions at one or a plurality of previously set mass-to-charge ratios. Alternatively, the MS unit 2 may repeatedly perform a scan measurement over a predetermined range of mass-to-charge ratios.

By the previously described measurement, a set of chromatogram data covering the period of time from the injection of a sample to the completion of the elution of the sample is obtained for each of the one or a plurality of mass-to-charge ratios. The data collected by one cycle of measurement performed for one sample are gathered into one data file and stored in the measurement data storage 4. When another sample is introduced into the LC unit 1 and chromatogram data are collected, those data are gathered into another data file and stored in the measurement data storage 4. Consequently, the same number of data files as the target samples are created and stored in the measurement data storage 4.

Figure 2:
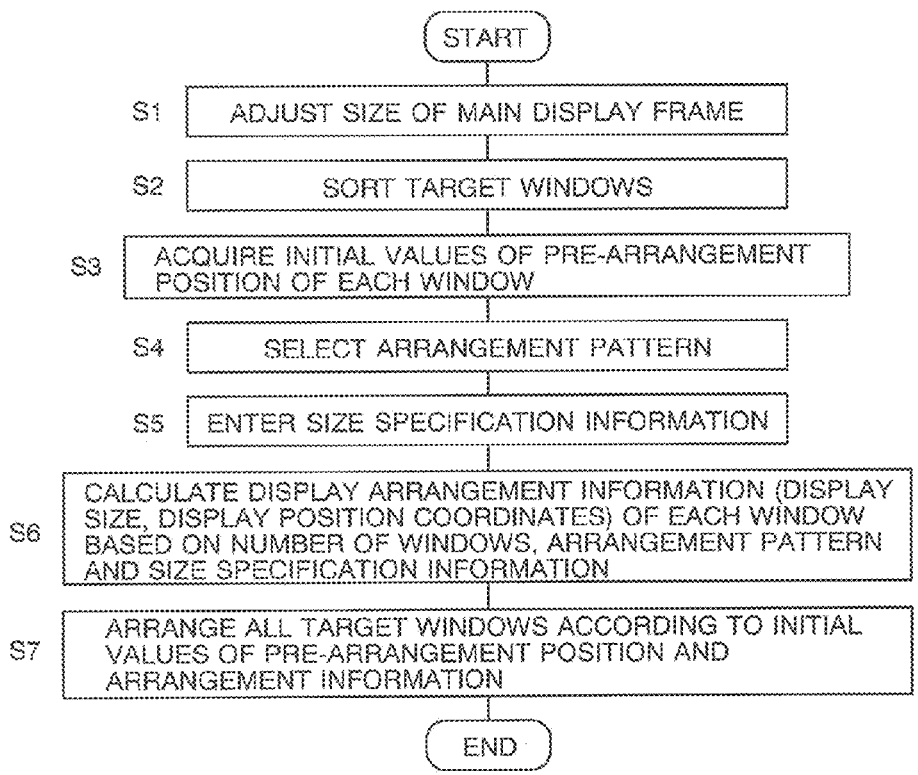
FIG. 2 is a flowchart showing a procedure of the window arrangement process for displaying graphs in the LC/MS system of the first embodiment.

A characteristic display control performed by the LC/MS system of the first embodiment is hereinafter described with reference to FIGS. 2 and 3A-3C. FIG. 2 is a flowchart showing a procedure of the window arrangement process for displaying graphs performed in the present system, and FIGS. 3A-3C are model diagrams showing one example of the window arrangement process for displaying graphs in the present system.

The following description deals with the example of arranging three mass spectra each of which is created by the graph creator 31 based on the data stored in the measurement data storage 4. Suppose that an operator has selected a data file to be visually checked through the input unit 6 and has entered a command for creating and displaying mass spectra at three arbitrary points in time. Then, the graph creator 31 reads appropriate data from the measurement data storage 4 and creates three mass spectra. The display controller 5 creates a display image in which the three mass spectra are respectively placed in three independent windows 101-103, as shown in FIG. 3A, and shows the image on the screen of the display unit 7. At this stage, the position and size of each window 101-103 are either the default values or the calculated values which depend, for example, on the position of the cursor. In the present example, it is assumed that the windows 101-103 initially have different sizes, as shown in FIG. 3A.

Initially, the operator appropriately adjusts the size of the main display frame 100 on the screen of the display unit 7 by performing a drag operation on an appropriate corner or side of the main display frame 100 with a pointing device (e.g. mouse) included in the input unit 6 (Step S1). Naturally, this Step S1 can be bypassed if the size adjustment of the main display frame 100 is unnecessary.

Next, the operator performs a drag and drop operation on the plurality of windows shown on the screen of the display unit 7 (three windows 101-103 in the case of FIG. 3A) with a pointing device so as to roughly arrange the windows 101-103 in a desired layout (Step S2). This sorting operation can be freely performed, for example, until the "OK" button (not shown) is pressed. It is preferable to additionally provide a "Cancel Fixation" button which can be used to cancel the fixed state and make the windows 101-103 once more freely movable even after the "OK" button has been pressed. In any case, after the sorted state is fixed, the pre-arrangement initial position input receiver 51 calculates the initial values of the pre-arrangement position based on the position of each of the windows 101-103 arranged on the screen (Step S3).

Specifically, one of the corners of each rectangular window can be designated as the point at which the positional coordinates should be acquired as the initial values of the pre-arrangement position. In the example of FIGS. 3A and 3B, the upper left corner of each window 101-103 (the position indicated by the circle in FIG. 3B) is designated as the positional coordinates acquisition point. After the windows 101-103 are moved to the positions as shown in FIG. 3B by means of the pointing device, the coordinates (X[s], Y[s]) (where s=0, 1 or 2) are acquired, as the initial values of the pre-arrangement position, from the positional coordinates (address) of the upper left corner of each window 101-103 on the display screen.

Next, when the operator performs a predetermined operation through the input unit 6, the arrangement pattern input receiver 52 shows an arrangement pattern specification dialogue 110, as shown in FIG. 4, on the screen of the display unit 7. On this arrangement pattern specification dialogue 110, the operator inputs the selection of a desired arrangement pattern by using a pointing device. Upon receiving this input of the selection, the arrangement pattern input receiver 52 sets the arrangement pattern (Step S4).

In the example shown in FIG. 4, the operator can select one of the four arrangement patterns. The "Stacked" and "Side by Side" options make the entire display area within the main display frame 100 equally divided in one direction (in the vertical or horizontal direction) into the same number of sections as the windows to be displayed. The "Overlapped" option makes windows laid on top of each other in a partially overlapped form. The "Arranged" option makes windows laid out in a two-dimensional pattern by dividing the entire display area within the main display frame 100 in rows and columns whose numbers are automatically determined according to the number of windows to be displayed. It is also possible to add other appropriate arrangement patterns. For example, it is possible to add an "Arranged in Specified Number of Rows and Columns" option, which allows users to numerically specify the number of rows and/or that of columns for a one-dimensional or two-dimensional arrangement of a plurality of windows. This example will be specifically described later.

In the case where the arrangement pattern which has been once selected is repeatedly used, the process of Step S4 can be bypassed. Step S4 will also be bypassed in the case where the arrangement pattern is specified beforehand and it isn't necessary for the operator to select it.

As shown in the present example, the windows, when arranged, normally have the same size (both width and height) and the process of Step S5 is bypassed. However, when any of the windows should be resized, an input from the operator is required. In such a case, the operator should enter the size specification information of each window through the input unit 6 (Step S5). Normally, the size specification information includes the ratio of the widths of a plurality of windows horizontally arranged in each row of the two-dimensional arrangement as well as the ratio of the heights of a plurality of windows vertically arranged in each column. However, this is not the only possible example. It is also possible to allow a size specification in which the width of the windows in the first column and the height of the windows in the first row are fixed, while the display areas of the other windows in the second and subsequent rows and columns are equally sized.

Subsequently, the display arrangement information calculator 53 calculates the display arrangement information of each window based on the selected arrangement pattern and the size specification information as well as the initial values of the pre-arrangement position of each window calculated in Step S3 (Step S6). Specifically, the display arrangement information includes the display size and display position coordinates of each window, and the display arrangement information calculator 53 determines the display size (width and height) of one window according to the arrangement pattern, the size specification information and the number of windows to be displayed. It also determines the positional relationship of the windows relative to each other based on the initial values of the pre-arrangement position of each window, and calculates the display position of each window from that positional relationship and the display size of each window. This display position means the positional coordinates of the positional coordinates acquisition point of each window after arrangement.

An example of the method for calculating the display arrangement information, i.e. the display size and the display position, in the display arrangement information calculator 53 is as follows: Suppose that the main display frame 100 after the size adjustment in Step S1 has a width of DX and a height of DY. Furthermore, consider the case where the initial values (X[s], Y[s]) of the pre-arrangement position three windows 101-103 (where s=0, 1, or 2) have been given as shown in FIG. 3B, and the "Stacked" option on the arrangement pattern specification dialogue 110 has been inputted as the arrangement pattern through the arrangement pattern input receiver 52. In this case, the display arrangement information calculator 53 initially computes the display size (width WX and height WY) of one window after arrangement by the following equations.

$$WX=DX$$

$$WY=DY/3$$

That is to say, in the case of a simple, one-column arrangement, the height of the main display frame 100 divided by the number of windows is used as the height of one window (WY), while the width of the main display frame 100 is directly used as the width of one window (WX).

Once the display size of one window is thus determined, the display areas to be respectively assigned to the three windows within the main display frame 100 can be fixed, and the position coordinates where each of the three windows should be located will also be automatically fixed. That is to say, each of the three areas formed by dividing the height of the entire display area within the main display frame 100 will be a display area assigned to one window, and the positional coordinates of the upper left corners of the three rectangular areas will be the coordinates of the three windows. The other information necessary for arranging the windows is the display order of the three windows, which can be easily determined in the case of a one-dimensional arrangement in the vertical (or horizontal) direction.

That is to say, the arrangement order in the vertical direction can be determined by sorting the three windows 101-103 in ascending order of the value of Y[s] of the initial coordinates (X[s], Y[s]) of their pre-arrangement positions (where s=0, 1, or 2). In the present example, since Y[0]<Y[2]<Y[1] (with the upper left corner of the main display frame 100 defined as the origin of the Y-axis coordinates), the display order of the three windows 101-103 will be Window[0], Window[2] and Window[1] in the top-to-bottom direction.

Using the display arrangement information calculated by the display arrangement information calculator 53, the arrangement execution processor 54 performs a resizing process for fitting each window 101-103 to the width (WX) and height (WY) of one window, followed by the process of sorting and arranging the windows according to their display position coordinates and display order. The result of these processes is eventually shown on the screen of the display unit 7 (Step S7). FIG. 3C shows the result of the arrangement in the previous example. Window[0], Window[2] and Window[1] are sequentially displayed in the top-to-bottom direction within the main display frame 100.

Thus, the present system can arrange windows 101-103 with the same relative positional relationship as visually confirmed by the operator in the process of manual sorting or other operations, as shown in FIG. 3B, without requiring the operator to be aware of the directions of the coordinate axes on the display screen, such as the X-axis (horizontal axis) or Y-axis (vertical axis).

The example shown in FIGS. 3A and 3B was a simple case in which three windows 101-103 were vertically arranged. A more complex example, in which a two-dimensional arrangement pattern with a specified number of rows and columns is used, will be hereinafter described with reference to FIGS. 5A and 5B.

Suppose that the main display frame 100 has a width of DX and a height of DY, as shown in FIG. 5A, and that the number of rows N and that of columns M (where both N and M are integers equal to or greater than two) have been specified as the arrangement pattern. In this case, the display size (width WX and height WY) of one window after arrangement can be calculated as follows.

$$WX=DX/M$$

$$WY=DY/N$$

That is to say, the height of one window (WY) is equal to the height of the main display frame 100 divided by the number of rows of the windows, while the width of one window (WX) is equal to the width of the main display frame 100 divided by the number of columns of the windows. Once the display size of one window is thus determined, the display areas to be respectively assigned to the M×N windows within the main display frame 100 will be fixed, and the position coordinates where each of the M×N windows should be located will also be automatically fixed. The other information necessary for arranging the windows is the display order of the windows in each of the vertical and horizontal directions.

For example, the display order of the M×N=Smax windows to be displayed can be determined as follows.

Suppose that the initial coordinates of the pre-arrangement position of Window[s] are denoted by (X[s], Y[s]) (where s=0, 1, 2, . . . or Smax−1), and the display order of an arrangement area Area[m][n] (where m=0, 1, 2, . . . or M−1; n=0, 1, 2, . . . or N−1) in the vertical and horizontal directions is denoted by (m[s], n[s]), where both m[s] and n[s] are integers. It should be noted that the symbol "//" used in the following description represents the mathematical operation of dividing one integer by another and obtaining the quotient as an integer.

(1) Initially, X[s] (s=0, 1, 2, . . . or Smax−1) are sorted in ascending order, and the order number of X[s] is stored in m[s]. The result is 0≤m[s]≤Smax−1.

(2) Next, the operation of m[s]←m[s]//N is performed to compose one column from N rows. As a result, the range of m[s] changes to 0≤m[s]≤M−1.

(3) Then, for each group of Y[s] having the same value of m[s], Y[s] are sorted and the order number is stored in n[s]. The result is 0≤n[s]≤N−1.

FIGS. 5A and 5B show an example of the process of arranging windows in the case of M=2 and N=2. Specifically, FIG. 5A shows the windows whose arrangement positions have been roughly set by the operator in Step S2. In this case, the previously described calculation steps will be as follows:

(1) All the windows are sorted in ascending order of X[s] (s=0, 1, 2 or 3). The order numbers of the sorted windows are m[0]=3, m[1]=1, m[2]=2 and m[3]=0.

(2) To compose one column from two rows, each of the m[s] values is divided by two. The result is m[0]=1, m[1]=0, m[2]=1 and m[3]=0.

(3) For each group of Y[s] having the same value of m[s], i.e. s=1 and 3 as well as s=0 and 2, Y[s] are sorted and the order numbers are stored in n[s]. The result is n[0]=1, n[1]=0, n[2]=0 and n[3]=1.

FIG. 5B shows the result obtained by arranging Window [s] in Area(m[s], n[s]). Thus, after the windows are manually arranged so as to roughly specify their relative positions in the horizontal and vertical directions, an arrangement result which maintains the specified positional relationship can be automatically obtained. When an operation error has been found, the error can be easily corrected by returning to Step S2, correcting only the position of the incorrectly placed window, and once more executing the arrangement operation.

FIGS. 6A and 6B show an example in which the previously described two-dimensional arrangement is used to display four mass spectra. In the arranged state shown in FIG. 6B, the upper row shows graphs of a target sample, the lower row shows those of a control sample, the right column shows mass spectra in which a precursor ion is present, and the left column shows MS/MS spectra obtained from that precursor ion. Such a window arrangement facilitates a comparison of MS/MS spectra or mass spectra between the target sample and the control sample.

In any of the previous examples, the windows arranged in the main display frame 100 have the same size. That is to say, the size specification information set in Step S5 is practically non-existent (default values are used) in those display examples. By contrast, an example which will be hereinafter described with reference to FIG. 7 is an arrangement example in which the size specification information is specified so that the windows to be displayed will have different sizes.

Similar to the example of FIGS. 5A and 5B, the arrangement pattern in the present example has two rows and two columns. However, as already noted, the display size can be made different for each window by setting size specification information, such as the ratio of the horizontal display sizes of a plurality of windows in each row and the ratio of the vertical display sizes of a plurality of windows in each column. In the example of FIG. 7, the first and second columns respectively have the widths of WX1 and WX2 (WX1≠WX2), and the first and second rows respectively have the heights of WY1 and WY2 (WY1≠WY2). Naturally, it is possible to make either WX1 and WX2 or WY1 and WY2 equal to each other.

Such a function of appropriately adjusting the window sizes on the arrangement display allows users, for example, to increase the window size and improve the visibility for a graph which is particularly noteworthy for comparison when there are a plurality of kinds of graphs to be displayed for each of the target and control samples. Such a layout not only improves the analyzing efficiency but also helps preparing a well-balanced, finely-presentable material in the case of directly using the displayed image in a printed report or similar document.

Figure 8:
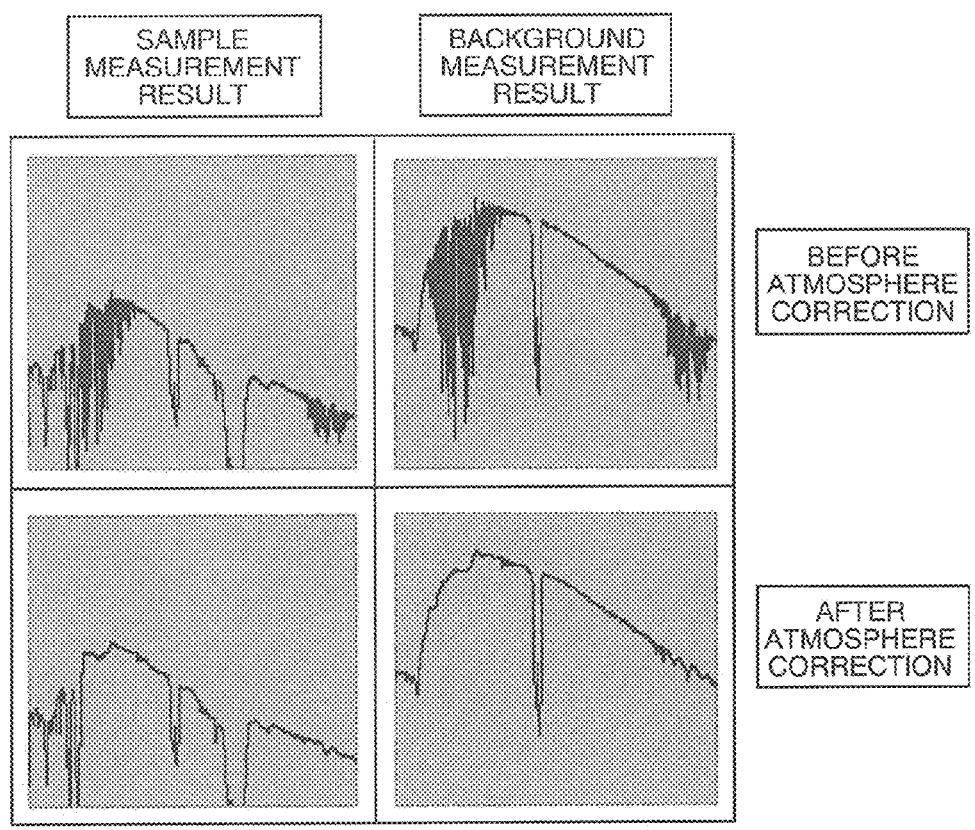
FIG. 8 shows one example of the process of two-dimensionally arranging a plurality of windows, with an absorption spectrum placed in each window, in the LC/MS system of the first embodiment.
Figure 9A:
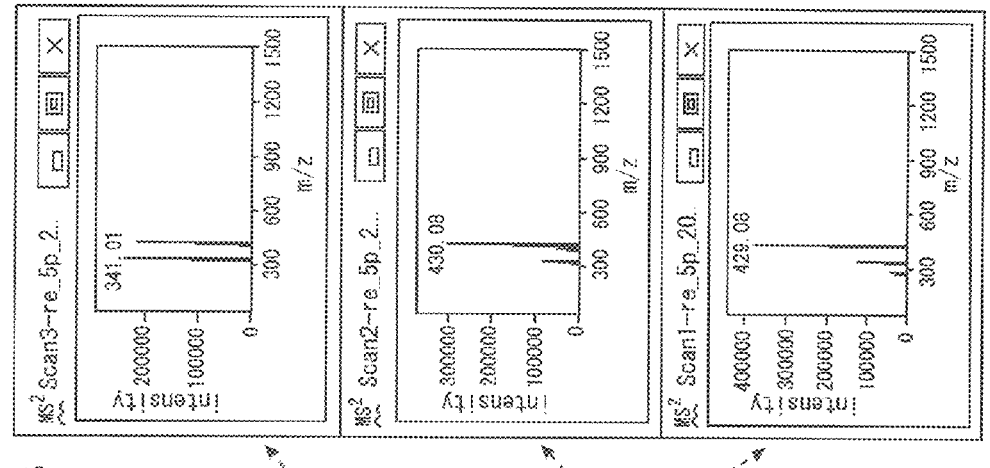
FIGS. 9A and 9B show one example of the process of arranging windows according to a conventional, common procedure.
Figure 9B:
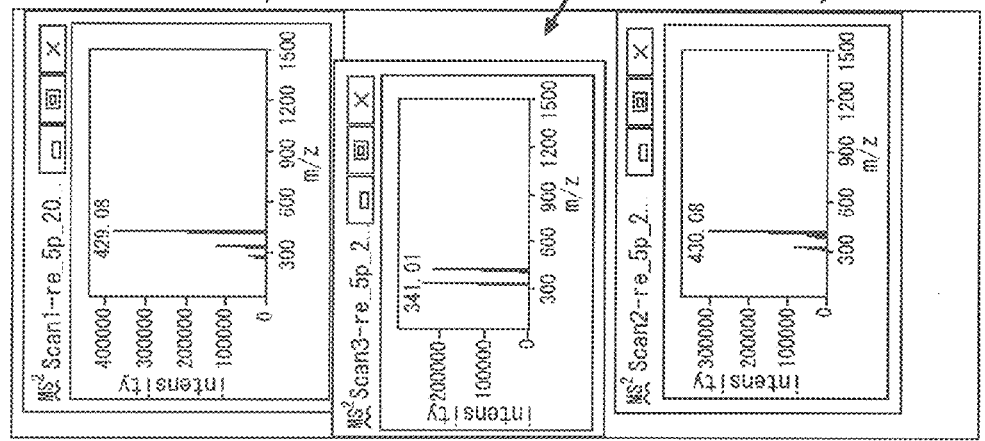

The previous embodiment was an example in which a process of displaying analysis data according to the present invention was applied to the display of LC/MS measurement data. The display arrangement by the present invention is also useful for the display of measurement data obtained by other kinds of analyzing systems. FIG. 8 shows a display example of absorption spectra created based on data obtained by a Fourier transform infrared spectrophotometer.

A Fourier transform infrared spectrophotometer is an apparatus for determining the absorbance-wavelength dependency of a sample by comparing the result of a sample measurement and that of a sample-less, background measurement. The apparatus has an atmosphere correction function for removing, from the measured result, influences of noise components which are constantly present in the atmosphere, such as moisture or carbon dioxide. In FIG. 8, the first and second columns are respectively assigned to the sample measurement and the background measurement, the first and second rows are respectively assigned to the results before and after the atmosphere correction, and an absorption spectrum created from each set of data is displayed at the column and row positions assigned to it.

Second Embodiment

In the LC/MS system of the first embodiment, the operation of Step S4, i.e. an input of the selection of the desired arrangement pattern by the operator, is required in the window arrangement process for displaying graphs. By contrast, an LC/MS system of another embodiment (second embodiment) of the present invention can provide an easy-to-view display for the operator without requiring the operator to make an input of the selection of the arrangement pattern beforehand.

Figure 10:
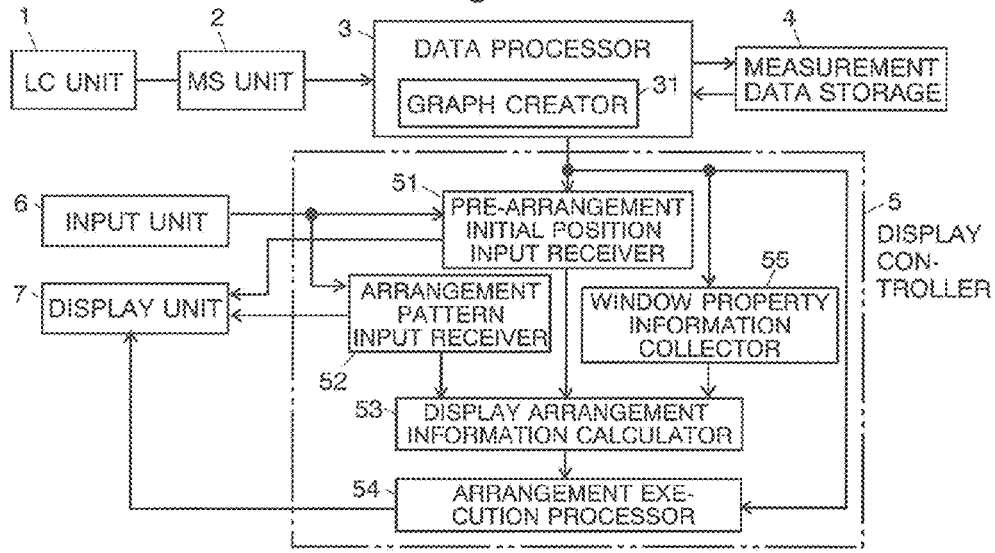
FIG. 10 is a configuration diagram showing the main components of an LC/MS system including a graph display processing system according to the second embodiment of the present invention.
Figure 11:
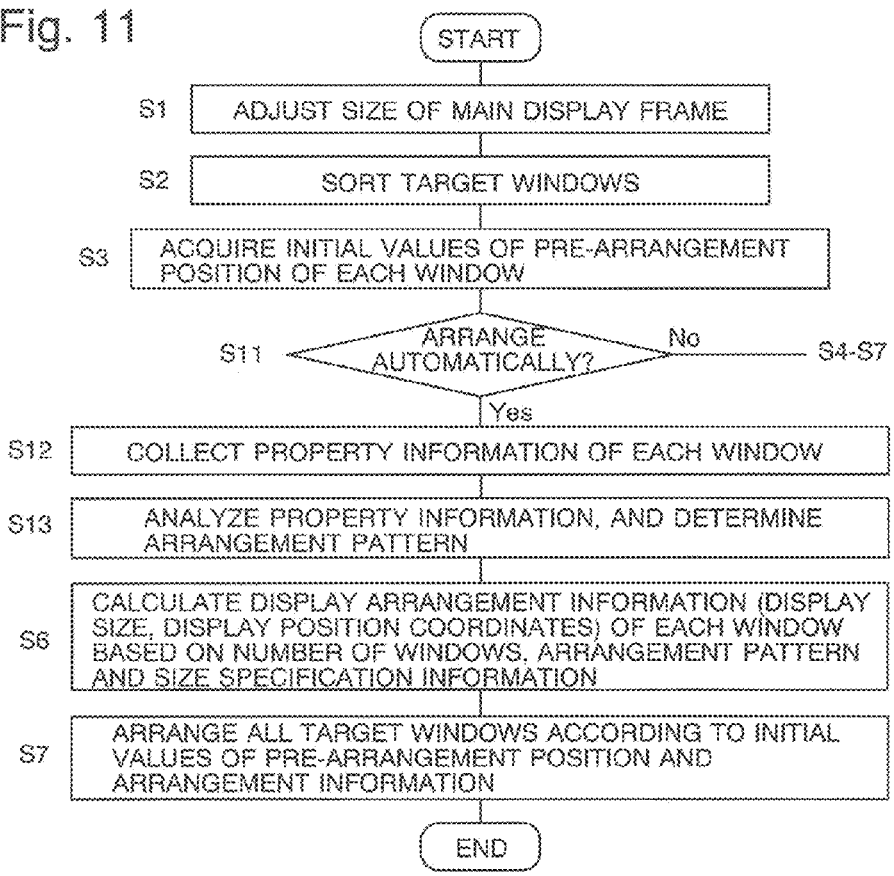
FIG. 11 is a flowchart showing a procedure of the window arrangement process for displaying graphs in the LC/MS system of the second embodiment.
Figure 12A:
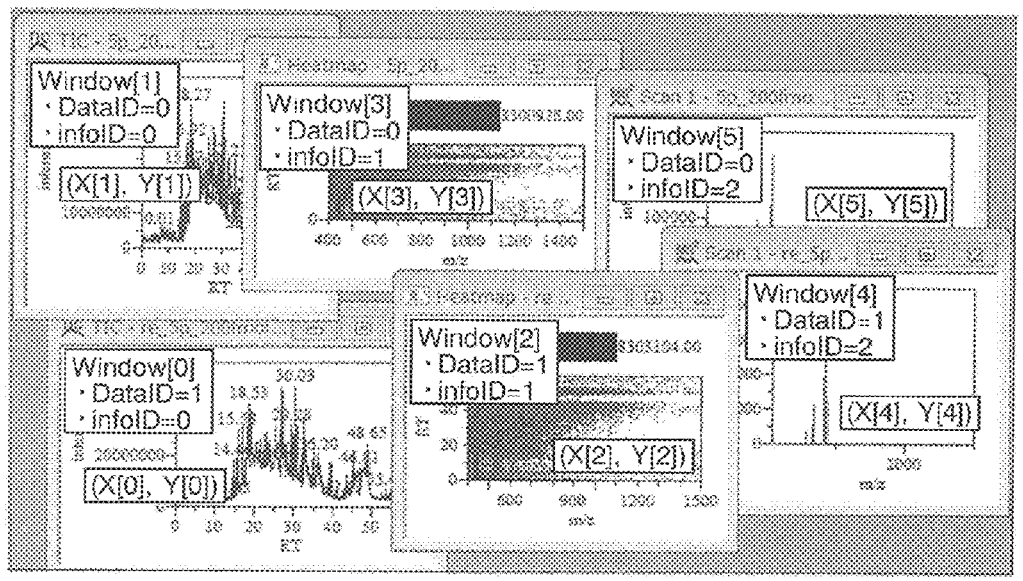
FIGS. 12A and 12B show one example of the process of two-dimensionally arranging a plurality of windows in the LC/MS system of the second embodiment.
Figure 12B:
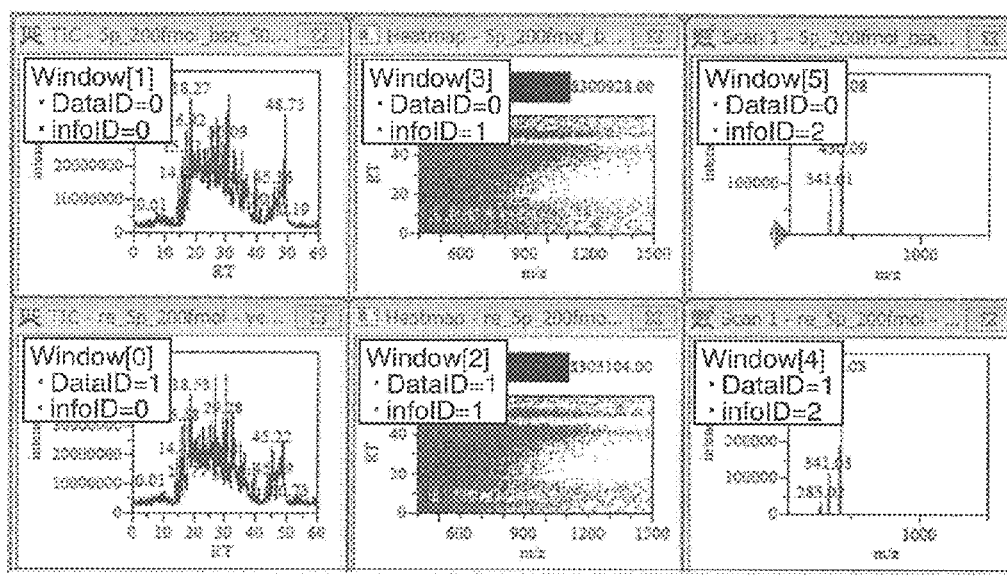

FIG. 10 is a configuration diagram showing the main components of an LC/MS system according to the second embodiment, FIG. 11 is a flowchart showing a procedure of the window arrangement process for displaying graphs performed in the present system, and FIGS. 12A and 12B show one example of the process of two-dimensionally arranging a plurality of windows in the present system. In FIG. 10, the components identical or corresponding to those used in the LC/MS system of the first embodiment shown in FIG. 1 are denoted by the same numerals and will not be described unless such descriptions are specifically required. In FIG. 11, the process steps identical to those performed in the LC/MS system of the first embodiment shown in FIG. 2 are denoted by the same step numbers.

In the system of the second embodiment, each window to be displayed has window property information as a property.

The window property information minimally includes an information type ID ("info ID") for identifying the type of information to be displayed in the window (i.e. the kind of graph), and a data type ID ("Data ID") for identifying the origin of the graph (e.g. the source of information). FIG. 17A shows the information type ID defined in the present example, and FIG. 17B shows the data type ID defined in the present example. The data type ID in FIG. 17B shows the kind of sample from which the data have been acquired. However, this is not the only possible choice; for example, the data type ID may be a piece of information which shows the type of device used for acquiring the data. These IDs can be arbitrarily defined beforehand.

As shown in FIG. 10, the system of the second embodiment includes one component which is not included in the system of the first embodiment, i.e. a window property information collector 55 for collecting the aforementioned window property information given to each of the windows to be arranged. Furthermore, the display arrangement information calculator 53 is modified so as to use the window property information collected by the window property information collector 55, in addition to the initial values of the pre-arrangement position and other information, when calculating the display arrangement information.

FIG. 12A shows a state in which a plurality of windows displayed on the screen of the display unit 7 (six windows in the example of FIG. 12A) have been roughly arranged in a desired layout by the operator. In other words, FIG. 12A shows a display on the screen when the process of Step S2 by a mouse operation or the like has been completed. "DataID" and "infoID" shown in FIG. 12A are the window property information shown in FIGS. 17A and 17B, which are given to each window. After the initial positions of the windows are fixed, the pre-arrangement initial position input receiver 51 calculates the initial values of the pre-arrangement position based on the position of each window arranged on the screen (Step S3). The arrangement pattern input receiver 52 determines whether or not the "automatic arrangement" function for setting the arrangement pattern without depending on an operation by the operator is enabled (Step S11). The "automatic arrangement" function can be set beforehand by operators, system administrators, or other users.

If the "automatic arrangement" function is not set (the result of Step S11 is "No"), the operation proceeds to the already described Step S4 in FIG. 2 and waits for an input of the selection of the arrangement pattern by the operator. If the "automatic arrangement" function is set beforehand (the result of Step S11 is "Yes"), the operation proceeds from Step S11 to Step S12, where the window property information collector 55 collects the window property information of all the windows arranged on the screen and sends the collected information to the display arrangement information calculator 53. In the case of FIG. 12A, for example, DataID=1 and infoID=0 are collected as the window property information for Window[0], and DataID=0 and infoID=0 are collected for Window [1].

Next, the display arrangement information calculator 53 analyzes all the collected window property information, and determines the number of necessary rows and columns as the arrangement pattern based on the analysis result (Step S13). Specifically, in the example of FIG. 12A, the six windows to be arranged have three different values of information type ID: "0", "1" and "2", and two different values of data type ID: "0" and "1." Accordingly, it is determined that the number of rows and that of columns of the two-dimensional arrangement necessary for the mutual comparison of the windows should be "3" and "2." However, there are two possible combinations of the numbers of rows and columns, i.e. (a) two rows and three columns or (b) three rows and two columns. One method for determining which combination should be chosen is to evaluate the difference in the initial position in the sorting direction of the windows having the same value for each of the two items of window property information, and to choose the combination having the smaller difference. A specific example of making this choice is hereinafter described, where Window [i] denotes each window (i=0, 1, 2, . . . or 5) and (X[i], Y[i]) denotes its initial position.

[Case A] Information type ID is sorted in the X-direction (horizontal direction) and data type ID is sorted in the Y-direction (vertical direction).

In this case, an initial position evaluation value ΔA is calculated by the following equation:

$$\Delta A = \sum_{info=0}^{infoN-1} XDiff(\text{info}) + \sum_{Data=0}^{DataN-1} YDiff(\text{Data})$$

where XDiff(info) is the difference between the maximum and minimum values of X[i] among Window[i] having the information type ID, and YDiff(Data) is the difference between the maximum and minimum values of Y[i] among Window[i] having the data type ID.

[Case B] Information type ID is sorted in the Y-direction and data type ID is sorted in the Y-direction.

In this case, an initial position evaluation value ΔB is calculated by the following equation:

$$\Delta B = \sum_{info=0}^{infoN-1} YDiff(\text{info}) + \sum_{Data=0}^{DataN-1} XDiff(\text{Data})$$

where YDiff(info) is the difference between the maximum and minimum values of Y[i] among Window[i] having the information type ID, and XDiff(Data) is the difference between the maximum and minimum values of X[i] among Window[i] having the data type ID.

In the example of FIG. 12A, since the following conditions are satisfied, ΔA is smaller than ΔB, so that it can be determined that [Case A] is more appropriate than [Case B]. As a result, the "two rows and three columns" form is chosen as the arrangement pattern.

$$\sum_{info=0}^{infoN-1} XDiff(\text{info}) < \sum_{Data=0}^{DataN-1} XDiff(\text{Data})$$

AND $$\sum_{Data=0}^{DataN-1} YDiff(\text{Data}) < \sum_{info=0}^{infoN-1} YDiff(\text{info})$$

With the arrangement pattern thus determined, it is now possible to perform the processes of Step S6 and S7 in a manner similar to the first embodiment to obtain the arrangement result as shown in FIG. 12B, using the automatically determined arrangement pattern instead of having the operator select the arrangement pattern as in the first embodiment.

In FIG. 12B, each column shows windows of the same information type; the first column is infoID=0 (chromatogram), the second column is infoID=1 (two-dimensional map), and the third column is infoID=2 (spectrum). On the other hand, each row shows windows of the same data type; the first row is DataID=0 (Treatment BSA) and the second row is DataID=1 (Control Sample).

Third Embodiment

Figure 13:
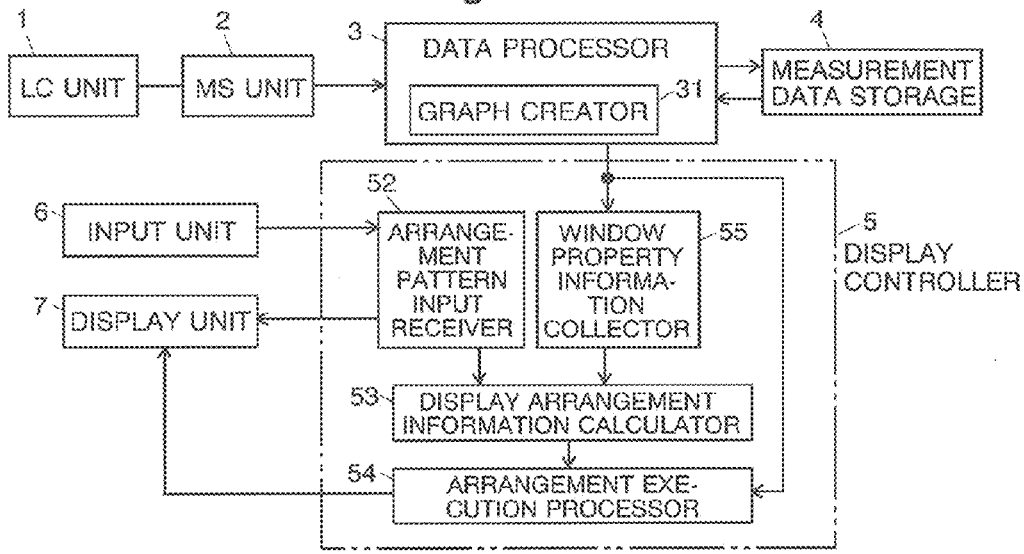
FIG. 13 is a configuration diagram showing the main components of an LC/MS system including a graph display processing system according to the third embodiment of the present invention.
Figure 14:
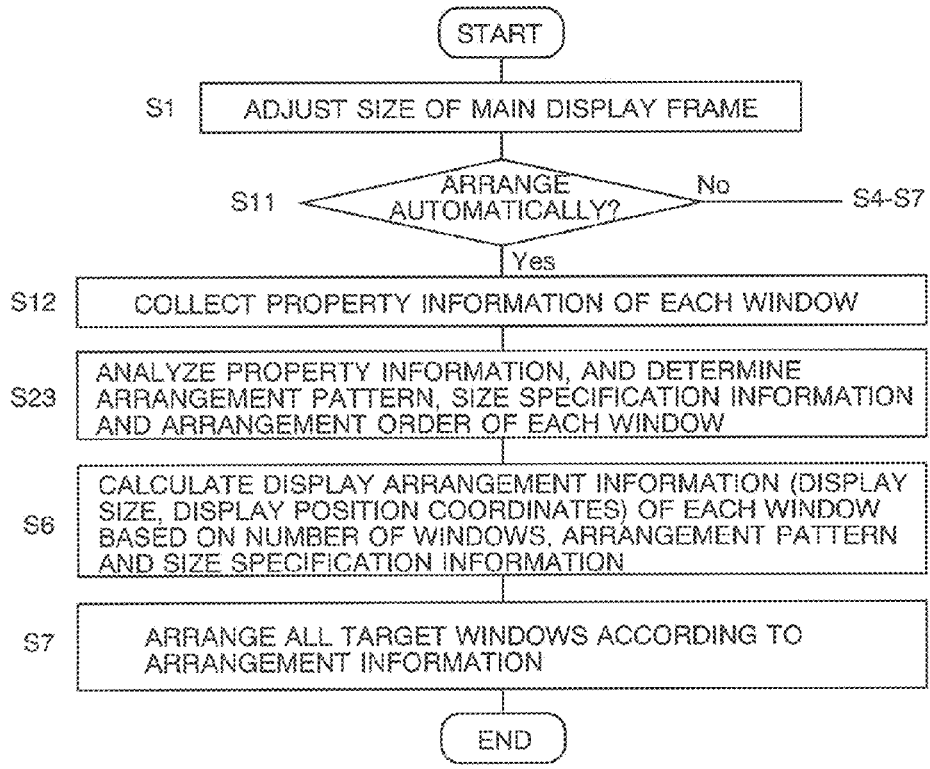
FIG. 14 is a flowchart showing a procedure of the window arrangement process for displaying graphs in the LC/MS system of the third embodiment.
Figure 15A:
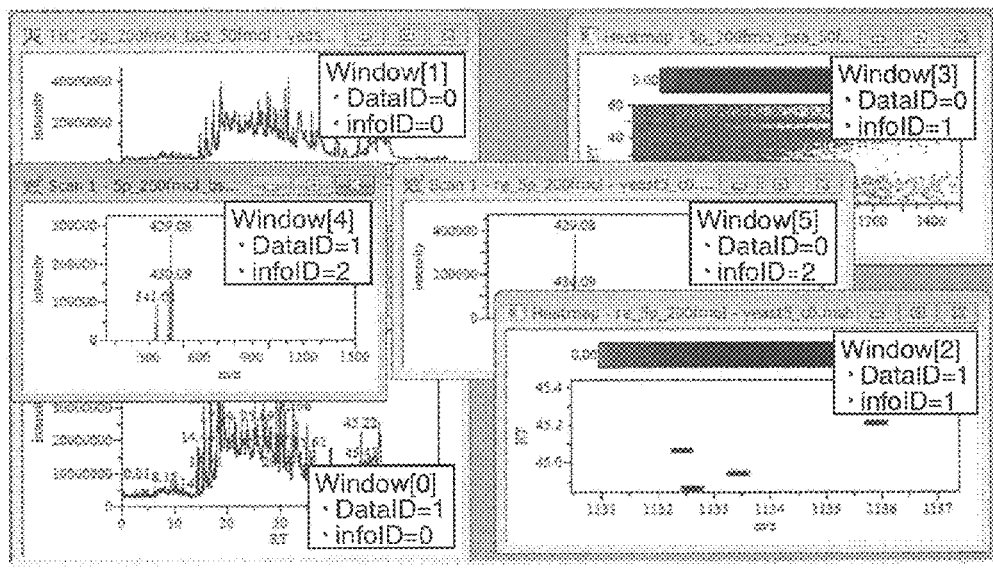
FIGS. 15A and 15B show one example of the process of two-dimensionally arranging a plurality of windows in the LC/MS system of the third embodiment.
Figure 15B:
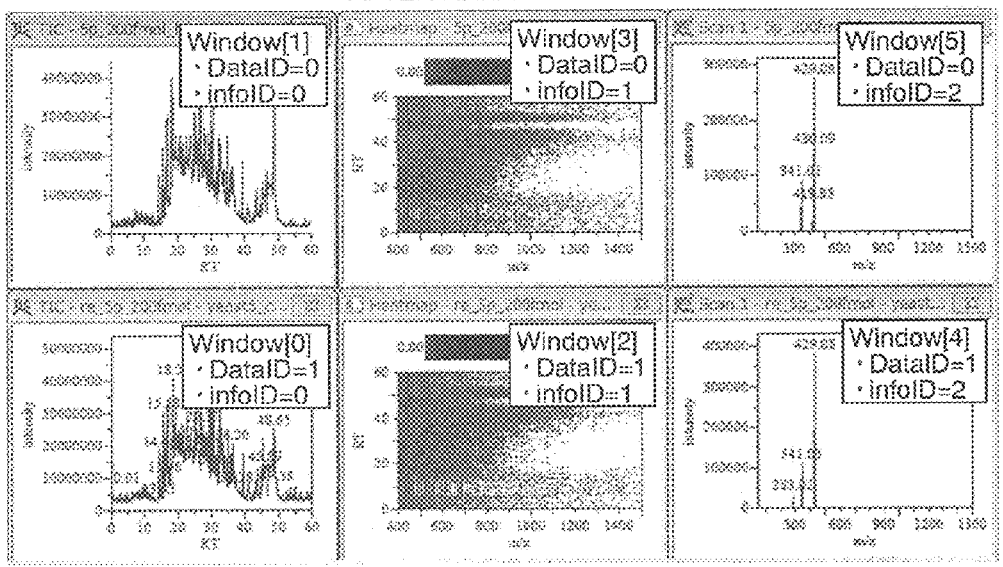

FIG. 13 is a configuration diagram showing the main components of an LC/MS system according to still another embodiment (third embodiment) of the present invention, FIG. 14 is a flowchart showing a procedure of the window arrangement process for displaying graphs performed in the present system, and FIGS. 15A and 15B show one example of the process of two-dimensionally arranging a plurality of windows in the present system. The system of the third embodiment even further reduces the time and labor of the operator than the system of the first or second embodiment. In other words, the system is designed to even further automate the process. Specifically, the operation corresponding to Step S2 in the flowchart shown in FIG. 11, i.e. the manual operation of roughly moving the windows to the desired positions, is omitted in the present system.

As shown in FIG. 13, the system of the third embodiment does not have the pre-arrangement initial position input receiver 51, which was provided in the system of the first or second embodiment. The display arrangement information calculator 53 has the function of automatically finding and setting an appropriate arrangement order of the windows based on the initial values of the pre-arrangement position of the windows and the window property information collected by the window property information collector 55, in addition to the previously described functions.

FIG. 15A shows one example of the display screen on which absolutely no window-moving operations by the operator have been performed. It is hereinafter assumed that the window property information given to each window is the same as the previously described one, as shown in FIGS. 17A and 17B.

If the arrangement pattern input receiver 52 has determined that the "automatic arrangement" function is set (the result of Step S11 is "Yes"), the window property information collector 55 collects the window property information of all the windows arranged on the screen and sends the collected information to the display arrangement information calculator 53 (Step S12). Next, the display arrangement information calculator 53 analyzes all the collected window property information, finds the number of necessary rows and columns as the arrangement pattern, based on the analysis result, and determines the arrangement order of the windows as follows (Step S23).

For example, suppose that the present system has the following "arrangement rules" previously defined for deciding the relationship between an arrangement direction and the information type ID or the data type ID included in the window property information, as well as for deciding the arrangement order:

<Rule 1> Information type ID should be sorted in the horizontal direction, and the data type ID should be sorted in the vertical direction.

<Rule 2> In both the horizontal and vertical directions, sorting should be performed in ascending order of the numerical value indicated by the ID concerned.

The analysis of the window property information should reveal that the six windows to be arranged have three different values of information type ID: "0", "1" and "2", and two different values of data type ID: "0" and "1." Accordingly, it is determined that the number of rows and columns of the two-dimensional display necessary for arranging the windows for mutual comparison should be the combination of "3" and "2". Next, the arrangement pattern is set by using the aforementioned "arrangement rules" without depending on the initial positions of the windows.

After the arrangement pattern is set, the processes of Step S6 and S7 are performed in a manner similar to the second embodiment to obtain the arrangement result as shown in FIG. 15B. It should be noted that, in the present case, the positions of the windows after arrangement are determined without taking into account the position of each window before the arrangement. Therefore, the windows are simply arranged according to the display arrangement information, without using the initial values of the pre-arrangement position.

In the example of FIG. 15B, the first column is infoID=0 (chromatogram), the second column is infoID=1 (two-dimensional map), and the third column is infoID=2 (spectrum). On the other hand, the first row is DataID=0 (Treatment BSA) and the second row is DataID=1 (Control Sample).

In case the previously defined "arrangement rules" do not agree with the demand of an operator, it is preferable to add a function for allowing operators to easily perform the operation of the "transpose rows and columns", "switch between ascending and descending orders" or the like before or after the arrangement. In any case, once the "arrangement rules" are defined, the arrangement result will be obtained without performing the process of Step S2 in FIGS. 2 and 11 for having the operator manually set the initial positions of the windows, even if the types of data and/or information to be displayed are changed, or if the number of data is changed.

FIG. 16 shows another example of the two-dimensional arrangement, in which there is only one value of information type ID: "2", while there are two values of data type ID: "0" and "1", each of which is accompanied by a subordinate value, i.e. the sub-data type ID. The information type ID and the data type ID included in the window property information are as shown in FIGS. 17A and 17B. The sub-data type ID, which is an item of the window property information, indicates the scan number, as shown in FIG. 17C, which denotes the order of a mass scan in a repetitive mass scan performed by a mass spectrometer.

In this case, an analysis of the window property information will reveal that the six windows to be arranged have a single value of information type ID: "2", two different values of data type ID: "0" and "1", as well as three different values of sub-data type ID: "0", "4" and "8." Therefore, it is possible to determine that the items of window property information to be sorted in the vertical or horizontal direction in the two-dimensional arrangement are the data type ID and the sub-data type ID, and that the number of rows and that of columns of the arrangement are the combination of "3" and "2." Based on this analysis result, the arrangement pattern can be automatically determined, and the windows can be arranged. As a result, a display as shown in FIG. 16 is obtained.

In the present example, there are the same number of values of sub-data type ID under each data type (i.e. there are three values of sub-data type ID: "0", "4" and "8" under both DataID=1 and DataID=2). However, this is not an indispensible condition. An appropriate arrangement pattern can be determined as long as the number of sub-data types to be displayed is known for each and every data type.

In general, it is possible to select appropriate items of window property information and achieve the automatic window arrangement by adopting the following rule: if there are three or more items of window property information, the two items of window property information having the largest and second largest numbers of different ID values among the windows to be displayed should be selected as the two axes for two-dimensionally arranging the windows.

It should be noted that any of the previously described embodiments is a mere example of the present invention, and any change, addition or modification appropriately made within the spirit of the present invention will naturally fall within the scope of claims of the present patent application.

EXPLANATION OF NUMERALS

1 . . . Liquid Chromatograph (LC) Unit
2 . . . Mass Spectrometer (MS) Unit
3 . . . Data Processor
31 . . . Graph Creator
4 . . . Measurement Data Storage
5 . . . Display Controller
51 . . . Pre-Arrangement Initial Position Input Receiver
52 . . . Arrangement Pattern Input Receiver
53 . . . Display Arrangement Information Calculator
54 . . . Arrangement Execution Processor
55 . . . Window Property Information Collector
6 . . . Input Unit
7 . . . Display Unit
100 . . . Main Display Frame
101-103 . . . Window
110 . . . Arrangement Pattern Specification Dialogue

The invention claimed is:

1. A graph display processing system for performing a process in which each of a plurality of graphs created on a basis of data collected by an analysis or measurement on a sample is placed in one of a plurality of windows and the windows are arranged in a previously determined display frame on a display screen, comprising:
   a) an initial position specifier for allowing an operator to independently move each of the plurality of windows in the display frame to an arbitrary position according to an operation by the operator;
   b) an initial position information acquirer for acquiring, as initial position information, information on a position of the plurality of windows after being moved by the initial position specifier;
   c) an arrangement pattern specifier for allowing the operator to perform an operation for specifying an arrangement pattern on the display screen;
   d) a post-arrangement display information calculator for calculating a display size and display position information of each window after arrangement, based on the initial position information of each window acquired by the initial position information acquirer and the arrangement pattern specified by the arrangement pattern specifier; and
   e) an arrangement processor for resizing each window according to the display size calculated by the post-arrangement display information calculator, and for displaying the resized windows in an arranged form according to the post-arrangement display position information calculated by the post-arrangement display information calculator.

2. The graph display processing system according to claim 1, further comprising a display frame specifier for allowing an operator to specify, on the display screen, the display frame,
   wherein the post-arrangement display information calculator partitions the display frame specified through the display frame specifier into a plurality of areas according to the number of windows to be displayed and the arrangement pattern, and calculates the display size and the display position information of each window.

3. The graph display processing system according to claim 1, wherein:
   the arrangement pattern specifier is configured so that size specification information to be used for adjusting the size of each area formed by partitioning the display frame can be specified; and
   the post-arrangement display information calculator partitions the display frame into a plurality of areas based on the size specification information.

4. The graph display processing system according to claim 1, wherein:
   the arrangement processor includes a display rule inverter for performing, according to a user operation, a process of transposing rows and columns of a two-dimensional arrangement pattern, or a process of inverting an arrangement order in at least one of row and column directions in a case of a two-dimensional arrangement pattern or an arrangement order in a case of a one-dimensional arrangement pattern.

5. The graph display processing system according to claim 2, wherein:
   the arrangement processor includes a display rule inverter for performing, according to a user operation, a process of transposing rows and columns of a two-dimensional arrangement pattern, or a process of inverting an arrangement order in at least one of row and column directions in a case of a two-dimensional arrangement pattern or an arrangement order in a case of a one-dimensional arrangement pattern.

6. The graph display processing system according to claim 3, wherein:
   the arrangement processor includes a display rule inverter for performing, according to a user operation, a process of transposing rows and columns of a two-dimensional arrangement pattern, or a process of inverting an arrangement order in at least one of row and column directions in a case of a two-dimensional arrangement pattern or an arrangement order in a case of a one-dimensional arrangement pattern.

7. A graph display processing system for performing a process in which each of a plurality of graphs created on a basis of data collected by an analysis or measurement on a sample is placed in one of a plurality of windows and the windows are arranged according to a specific arrangement pattern in a previously determined display frame on a display screen, comprising:
   a) an initial position specifier for allowing an operator to independently move each of the plurality of windows in the display frame to an arbitrary position according to an operation by the operator;
   b) an initial position information acquirer for acquiring, as initial position information, information on a position of the plurality of windows after being moved by the initial position specifier;
   c) a post-arrangement display information calculator for calculating a display size and display position information of each window after arrangement, based on the initial position information of each window acquired by the initial position information acquirer and the arrangement pattern specified beforehand; and d) an arrangement processor for resizing each window according to the display size calculated by the post-arrangement display information calculator, and for displaying the resized windows in an arranged form according to the post-arrangement display position information calculated by the post-arrangement display information calculator.

8. The graph display processing system according to claim 7, wherein:

the arrangement processor includes a display rule inverter for performing, according to a user operation, a process of transposing rows and columns of a two-dimensional arrangement pattern, or a process of inverting an arrangement order in at least one of row and column directions in a case of a two-dimensional arrangement pattern or an arrangement order in a case of a one-dimensional arrangement pattern.

9. A graph display processing system for performing a process in which each of a plurality of graphs created on a basis of data collected by an analysis or measurement on a sample is placed in one of a plurality of windows and the windows are arranged in a previously determined display frame on a display screen, comprising:

a) an initial position specifier for allowing an operator to independently move each of the plurality of windows in the display frame to an arbitrary position according to an operation by the operator;

b) an initial position information acquirer for acquiring, as initial position information, information on a position of the plurality of windows after being moved by the initial position specifier;

c) an arrangement pattern determiner for collecting window property information for each and every one of the plurality of windows shown on the display screen, the window property information given to each window beforehand and including at least information indicating a kind and origin of the graph placed in each window, and for determining an arrangement pattern based on the collected window property information corresponding to the plurality of windows;

d) a post-arrangement display information calculator for calculating a display size and display position information of each window after arrangement, based on the initial position information of each window acquired by the initial position information acquirer and the arrangement pattern determined by the arrangement pattern determiner; and e) an arrangement processor for resizing each window according to the display size calculated by the post-arrangement display information calculator, and for displaying the resized windows in an arranged form according to the post-arrangement display position information calculated by the post-arrangement display information calculator.

10. The graph display processing system according to claim 9, wherein:

the arrangement processor includes a display rule inverter for performing, according to a user operation, a process of transposing rows and columns of a two-dimensional arrangement pattern, or a process of inverting an arrangement order in at least one of row and column directions in a case of a two-dimensional arrangement pattern or an arrangement order in a case of a one-dimensional arrangement pattern.

11. A graph display processing system for performing a process in which each of a plurality of graphs created on a basis of data collected by an analysis or measurement on a sample is placed in one of a plurality of windows and the windows are shown on a display screen, comprising:

a) an arrangement rule determiner for collecting window property information for each and every one of the plurality of windows shown on the display screen, the window property information given to each window beforehand and including at least information indicating a kind and origin of the graph placed in each window, for determining an arrangement pattern based on the collected window property information corresponding to the plurality of windows, and for determining an arrangement order of each window based on the window property information;

b) a post-arrangement display information calculator for calculating a display size and display position information of each window after arrangement, based on the arrangement pattern and the arrangement order determined by the arrangement rule determiner; and c) an arrangement processor for resizing each window according to the display size calculated by the post-arrangement display information calculator, and for displaying the resized windows in an arranged form according to the post-arrangement display position information calculated by the post-arrangement display information calculator.

12. The graph display processing system according to claim 11, wherein:

the arrangement processor includes a display rule inverter for performing, according to a user operation, a process of transposing rows and columns of a two-dimensional arrangement pattern, or a process of inverting an arrangement order in at least one of row and column directions in a case of a two-dimensional arrangement pattern or an arrangement order in a case of a one-dimensional arrangement pattern.

* * * * *